United States Patent [19]
Konrad

[11] Patent Number: 5,897,508
[45] Date of Patent: *Apr. 27, 1999

[54] HOLDING DEVICE FOR A BLOOD SAMPLE REMOVAL TUBULE OF A BLOOD REMOVAL DEVICE

[75] Inventor: Franz Konrad, Regau, Austria

[73] Assignee: C.A. Greiner & Söhne Gesellschaft m.b.H., Kremsmünster, Austria

[ * ] Notice: This patent issued on a continued prosecution application filed under 37 CFR 1.53(d), and is subject to the twenty year patent term provisions of 35 U.S.C. 154(a)(2).

[21] Appl. No.: 08/652,554
[22] PCT Filed: Dec. 14, 1994
[86] PCT No.: PCT/AT94/00196
   § 371 Date: May 31, 1996
   § 102(e) Date: May 31, 1996
[87] PCT Pub. No.: WO95/16395
   PCT Pub. Date: Jun. 22, 1995

[30] Foreign Application Priority Data

Dec. 16, 1993 [AT] Austria .................................. 2559/93

[51] Int. Cl.⁶ ............................................................ A61B 5/00
[52] U.S. Cl. .......................... 600/573; 600/578; 604/192
[58] Field of Search ..................................... 600/573, 576, 600/577, 578, 579, 192, 240

[56] References Cited

U.S. PATENT DOCUMENTS

| 4,819,659 | 4/1989 | Sitar ......................................... 128/764 |
| 5,505,721 | 4/1996 | Leach et al. ............................. 128/763 |

FOREIGN PATENT DOCUMENTS

| 0 029 126 | 5/1981 | European Pat. Off. . |
| 0 031 900 | 7/1981 | European Pat. Off. . |
| 0 106 290 | 4/1984 | European Pat. Off. . |
| 0 286 087 | 10/1988 | European Pat. Off. . |
| 0 323 903 | 7/1989 | European Pat. Off. . |
| 0 364 777 | 4/1990 | European Pat. Off. . |
| 0364777 | 4/1990 | European Pat. Off. . |
| 0 478 459 | 4/1992 | European Pat. Off. . |
| 0478459A1 | 4/1992 | European Pat. Off. . |
| 0 489 977 | 6/1992 | European Pat. Off. . |
| 0489977A1 | 6/1992 | European Pat. Off. . |
| WO88/04154 | 6/1988 | WIPO . |
| WO89/10723 | 11/1989 | WIPO . |
| WO92/04867 | 4/1992 | WIPO . |

*Primary Examiner*—John G. Weiss
*Assistant Examiner*—Virendra Srivastava
*Attorney, Agent, or Firm*—Collard & Roe, P.C.

[57] ABSTRACT

The invention describes a holding device (2) for a blood sample removal tubule (3) of a blood removal device (1) with a receiving vessel (11) for a front end of the blood sample removal tubule (3), closed by a closure device (39), with a needle holder (22). In the needle holder (22) a cannula (23) is mounted, directed towards the opened front side (12) of the receiving vesel (11), and projects in the direction thereof. A through-flow opening (53) is connected by means of a connecting canal (32), constructed between the needle bolder (22) and a front wall (17) of the receiving vessel (11), with a removal needle (5) of a needle arrangement (4), arranged eccentrically to a central longitudinal axis (13) of the receiving chamber (15). Between the connecting canal (32) and a receiving chamber (15) of the receiving vessel (11), an openable valve arrangement (52) is arranged as required. This valve arrangement (52) is formed fly a hose valve (36) or flap valve arranged between the cannula (23) and the receiving chamber (15) and/or the connecting canal (32). The cannula (23) is preferably arranged concentrically to the receiving vessel (11). A through-flow canal (31) opens between the cannula (23) and an outer wall of the receiving vessel (11) into the connecting canal (32).

20 Claims, 5 Drawing Sheets

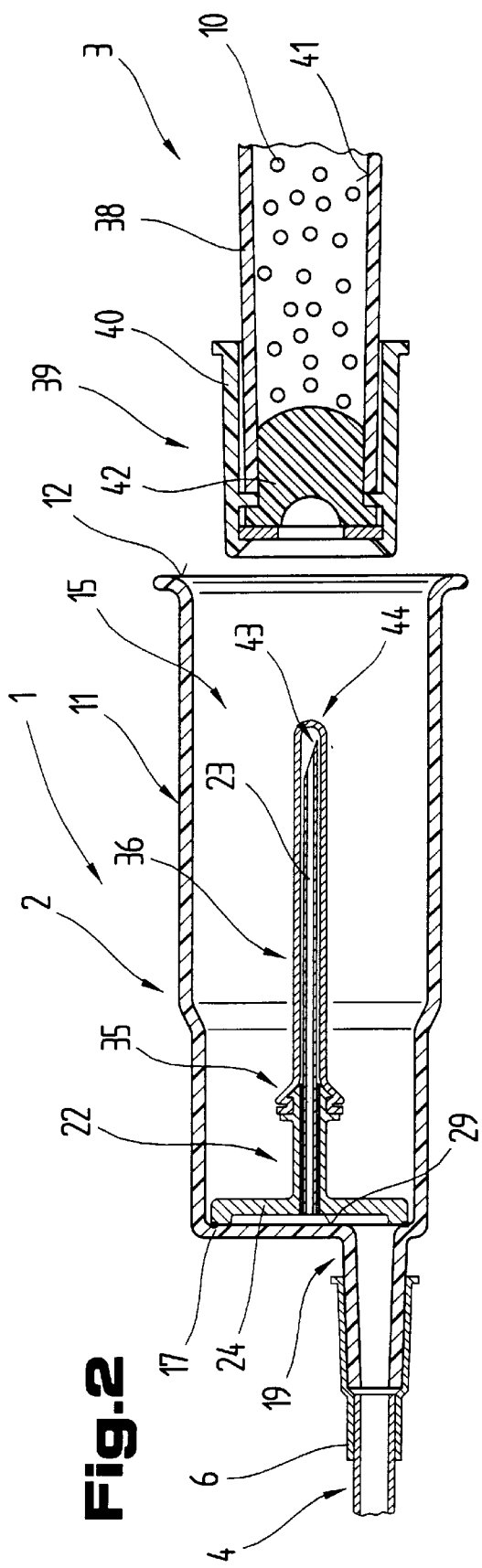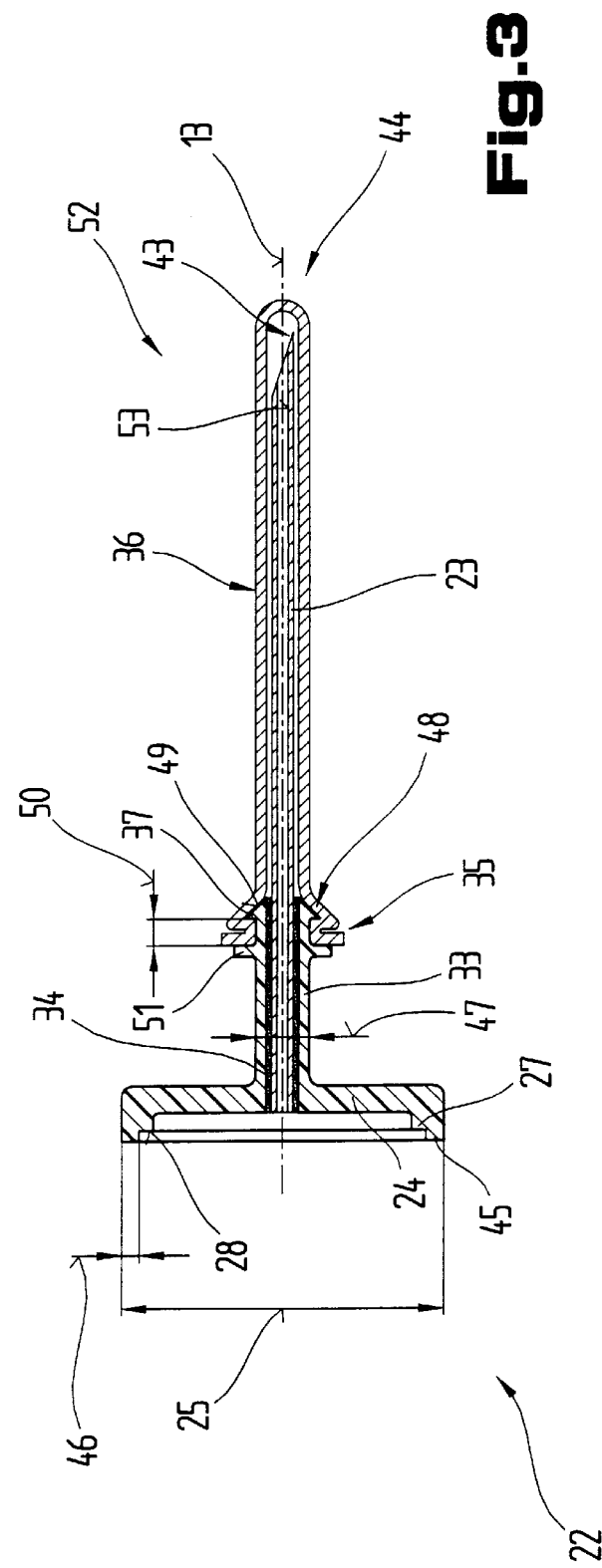

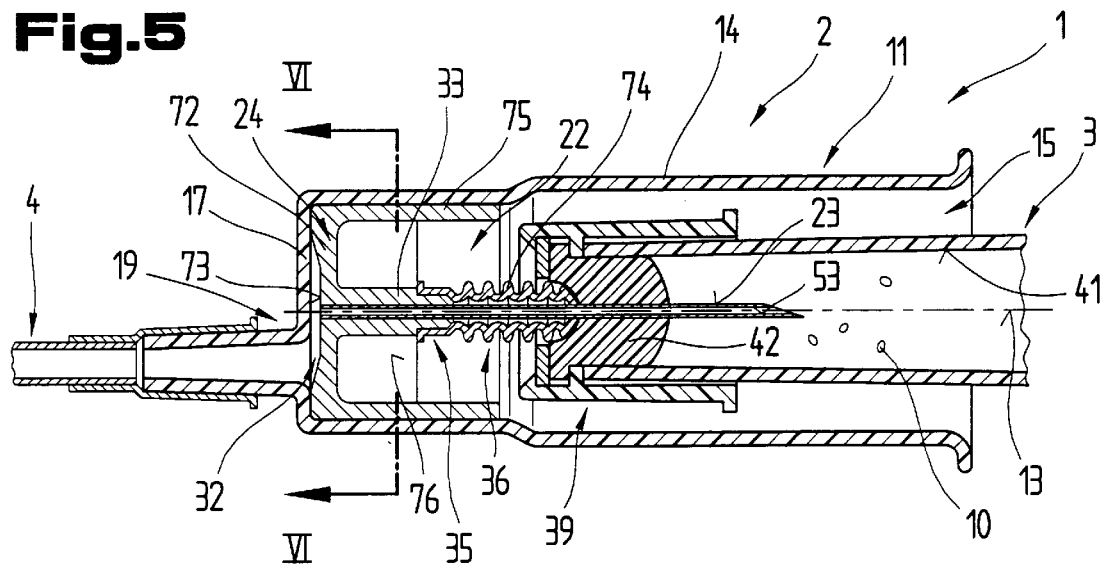
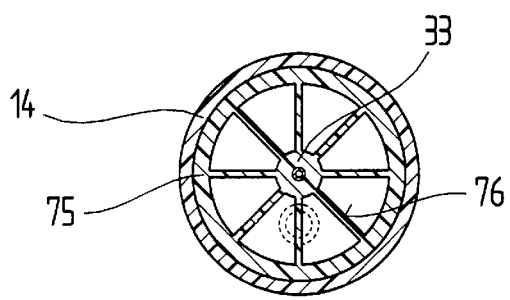
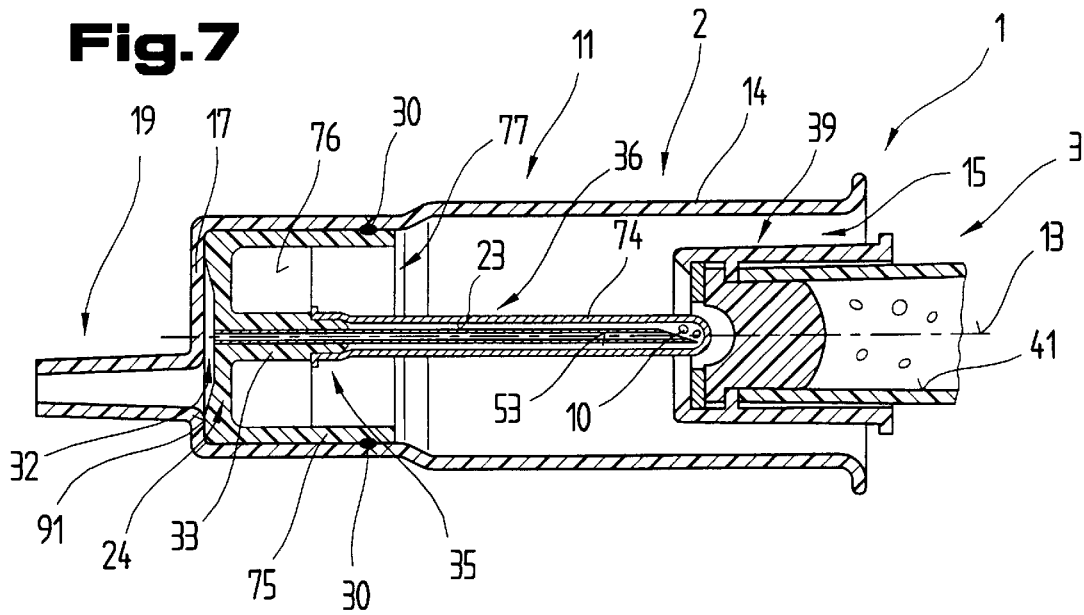

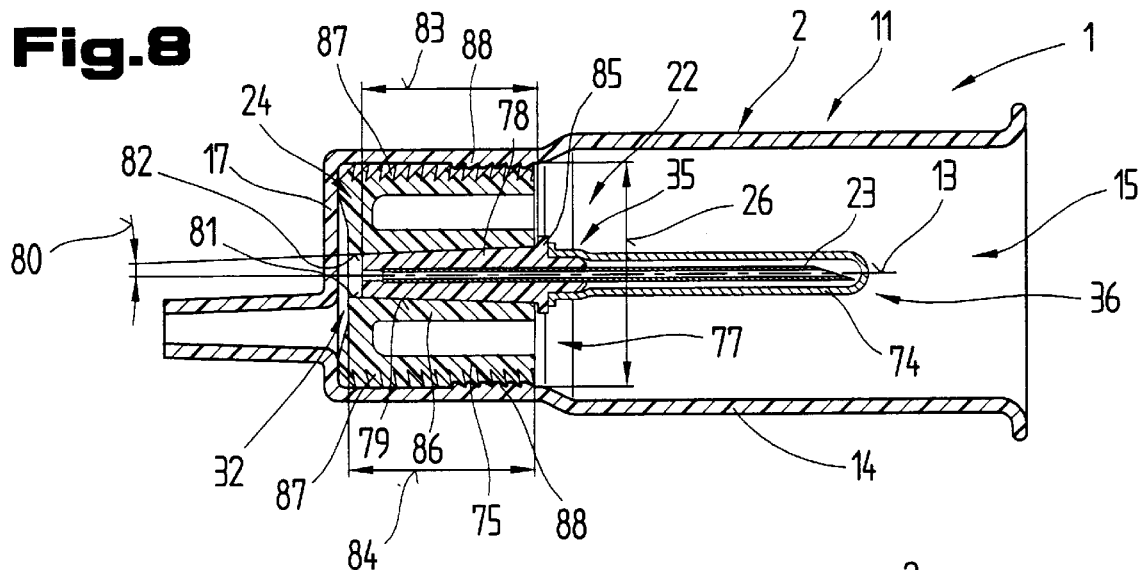
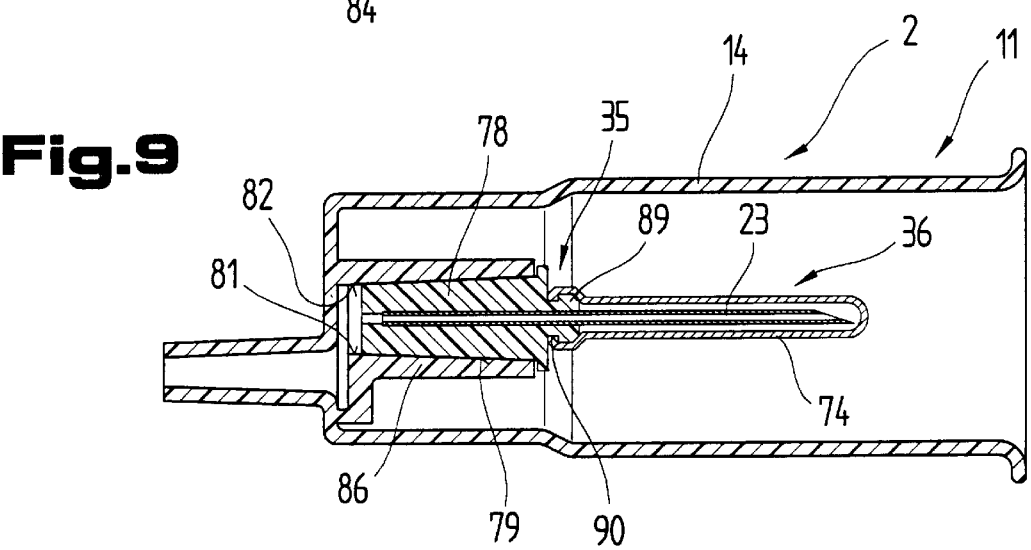
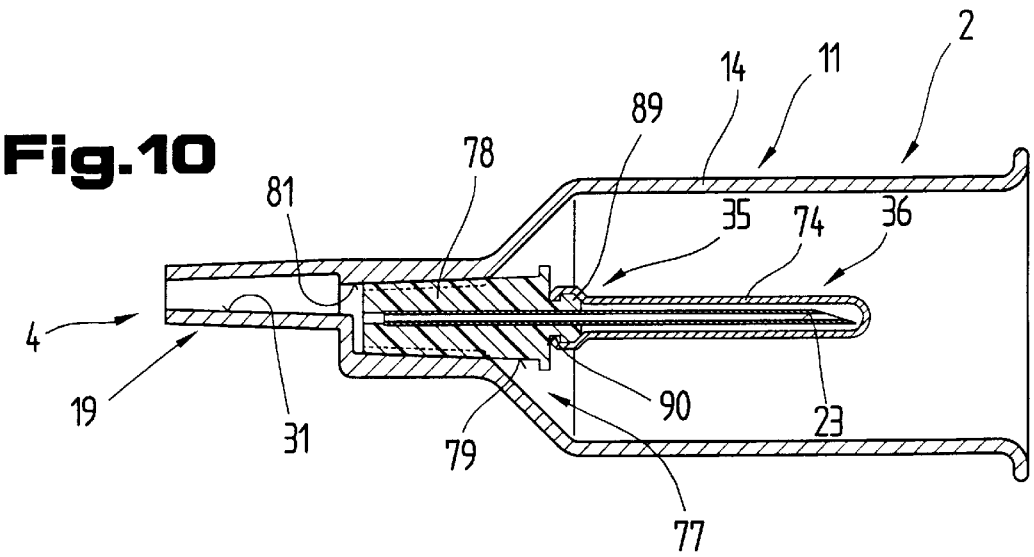

HOLDING DEVICE FOR A BLOOD SAMPLE REMOVAL TUBULE OF A BLOOD REMOVAL DEVICE

BACKGROUND OF THE INVENTION

1. Field of the Invention

The invention relates to a holding device for a blood sample removal tubule.

2. Description of the Prior Art

Holding devices for blood sample removal tubules of a blood removal device are known from WO 89/10723, for example, which has a receiving vessel for a front end of the blood sample removal tubule. The blood sample removal tubule is closed at its front end by a closure device. In the receiving vessel, a needle holder is arranged for a cannula, which projects in the direction of an opened front side of the receiving vessel and the through opening of which is connected with a removal needle of a needle arrangement via a connecting canal constructed between the needle holder and the front wall of the receiving vessel. This removal needle is arranged eccentrically to a central longitudinal axis of the receiving chamber. Between the connecting canal and a receiving chamber of the receiving vessel, a valve arrangement is provided which is able to be opened as required. This valve arrangement is formed by the cannula and the needle holder. For this, the cannula is mounted so as to be adjustable in a bore of the needle holder in the longitudinal direction of the central longitudinal axis of the receiving vessel. To limit the adjustment movement, the cannula is provided in its end arranged in the connecting canal with a stop projecting over its outer periphery in a radial direction. For this, the cannula is squeezed together in its end facing the connecting canal and is bent around through 90° and has in the side wall an opening through which the through-flow opening is connected in a conducting manner with the connecting canal. A disadvantage here is that through the cannula mounted displaceably in the needle holder, the gas tightness between the removal needle and the blood sample removal tubule can only be achieved with difficulty and in addition to permeability, which partially also leads to an emergence of the blood, in many cases the vacuum of the blood sample removal tubule can not be used for the removal of blood.

Further blood removal devices are known from U.S. Pat. No. 4,819,659, European patents 0 478 459; 0 286 087 and 0 364 777, in which the cannula is constructed in each case so as to be continuous and is mounted in a needle holder or in a guide sleeve. In so doing, the cannula represents at the same time at one end the removal needle and at the other end the puncture needle into the closure plug of the blood sample tubule. In addition, the cannula is surrounded at the end facing the blood sample removal tubule with a valve arrangement, which is able to be opened as required, in the form of a hose valve. In these embodiments of the removal device, it is not possible to separate the holding device from the needle arrangement in order, for example, to be able to supply an infusion to the patient, without having to remove the needle. Furthermore, an increased safety risk exists for the user in that owing to the already fixedly arranged removal needle, injuries can already occur during the preparation of the holding device. An additional disadvantage is also produced by the fact that the removal needle, which is constructed so as to be continuous, is arranged centrally to the holding device, whereby owing to the greater inclined position of the entire removal device on piercing into the vein, an increased additional risk of injury exists.

SUMMARY OF THE INVENTION

The present invention addresses the problem of creating a valve arrangement for a blood removal device in the receiving vessel, which makes possible a gas-tight connection between the cannula and the removal needle.

This problem is solved with a holding device for a blood sample removal tubule, which comprises a receiving vessel comprising a cylindrical jacket having a central longitudinal axis and an open end, and a front wall closing an end of the receiving vessel opposite the open end, the cylindrical jacket and the front wall defining a receiving chamber. A holding part is connected to the front wall of the receiving vessel and projects therefrom in a direction facing away from the cylindrical jacket, the holding part being arranged eccentrically with respect to the central longitudinal axis and defining a flow-through canal. A cannula has one end facing the front wall of the receiving vessel and an opposite end facing the open end of the receiving vessel, the cannula defining a flow-through bore. A holder for the cannula comprises a carrier part having a periphery connected to the receiving vessel in a gas- and fluid-tight manner by means extending along the periphery of the carrier part, and a carrier holding the cannula in a fixed position and in a gas- and fluid-tight manner, the opposite end of the cannula projecting beyond the carrier, the carrier part of the holder and the front wall of the receiving vessel defining a connecting canal therebetween, the connecting canal connecting the flow-through canal of the holding part with the flow-though bore of the cannula. A selectively openable valve arrangement is arranged between the connecting canal and the receiving chamber, the valve arrangement comprising a hose valve arranged between the cannula and the receiving chamber.

It is advantageous in this construction that through the use of a cannula which is fixedly inserted into the needle holder, only with a corresponding fastening of the needle holder in the receiving vessel can a definitive connecting and sealing layer be created, with which a fluid- and gas-tight connection can be brought about in a simple manner between the cannula and the removal needle. Thereby a suction of foreign air from the receiving chamber of the receiving vessel into the blood sample removal tubule is also not possible. In addition to this is the fact that also the piercing of the closure device in the blood sample removal tubule with the cannula is facilitated and the risk of injury to the patient's veins is eliminated because jerky stresses, as occurred in the known valve arrangement with the movement of the needle relative to the receiving vessel or when the needle strikes against the receiving vessel, are avoided. In addition to this is the fact that with the use of a hose valve, the through-flow opening of the cannula is only freed after its introduction into the closure device of the blood sample removal tubule or is closed simultaneously with the removal of the cannula from the closure device again, so that the emergence of blood or of another body fluid removed with the blood sample removal tubule and consequently the risk of an infection can be impeded or ruled out entirely. When the blood sample removal tubule is actuated, the through flow of blood or of the other body fluid is only eliminated after the penetration of the penetration device of the blood sample removal tubule and, on the other hand, a further through flow of the blood is already eliminated before the cannula has emerged from the closure device of the blood sample removal tubule.

It is advantageous for the carrier part of the holder to have an outer diameter which is smaller than an inner diameter of an adjacent portion of the cylindrical jacket of the receiving vessel because therewith a problem-free positioning of the carrier part is possible on the front wall of the receiving vessel and hence over the entire periphery the production of a gas-tight connection is possible even in the case of greatly changing tolerances in the outer and inner diameters. A tight connection between the carrier part and the receiving vessel is achieved if the carrier part is disc-shaped.

If the carrier part of the holder has an annular collar projecting from the carrier part towards the front wall of the receiving vessel, a defined bearing zone of the carrier part on the front wall of the receiving vessel is achieved, which favors a gas-tight connection and in addition, at the same time, makes possible by simple means the production of a connecting canal.

If the flow-through canal of the holding part opens into the connecting canal in an area defined by the annular collar, an additional transition site is prevented between individual parts of the blood removal device and hence the tightness of the entire system is considerably improved.

It is possible that despite a thin, disc-like construction of the carrier part, a solid mounting of the cannula, also receiving higher tensile and compressive forces, can be achieved in the receiving vessel.

Using a hose valve which is a fluid-tight casing having the shape of a stocking makes possible at the same time a simple production of the hose valve, in particular of the fastening of the fluid-tight casing thereof.

A simple fastening of the casing of the hose valve can be achieved with a holding device on an end of the carrier facing the open end of the receiving vessel for retaining an open end of the fluid-tight casing. The holding device is preferably a frusto-conical holding nose tapering inwardly towards the open end of the receiving vessel.

The carrier part of the holder may comprise a portion projecting therefrom towards the open end of the receiving vessel, the projecting carrier part portion defining a frusto-conical bore widening towards the open end, and the carrier is held in the frusto-conical bore and has a stop flange, the bore having a length exceeding that of the carrier. With the use of a press fit a firm fit can be reliably achieved between the holder and the receiving vessel. An incorporation of the needle holder can be achieved only after the gas-tight insertion of the carrier part into the receiving chamber.

If the receiving chamber has a receiving space for the carrier part of the holder and the carrier part is securely held in the receiving space, the remaining part of the receiving chamber can be produced with a greater tolerance and hence at a more favorable cost.

It is advantageous if the carrier part of the holder has a cylindrical portion projecting from a circumference of the carrier part towards the open end of the cylindrical jacket along an inner surface of the cylindrical jacket, and a gas-tight means connects the cylindrical carrier part portion to the cylindrical jacket. With the use of a pot-like carrier part with a cylindrical outer jacket, a gas-tight seal can be achieved between the latter and the receiving chamber or the cylinder jacket.

With a bearing surface for the carrier part of the holder, the bearing surface extending substantially perpendicularly to the central longitudinal axis between the flow-through canal of the holding part and the cylinder jacket, even with an eccentric removal needle inserted to the central longitudinal axis of the removal vessel, an intensive, gas-tight seal can be achieved between the carrier part and the removal vessel.

Through the use of a plastic for the carrier part and/or the receiving vessel, in addition to a sufficient inherent stability, a firm fit and a tight connection between the carrier part is ensured.

If the carrier part has peripheral sealing lips extending in a radial direction, the sealing lips in a relaxed state having an outer diameter exceeding an inner diameter of the receiving space, in an advantageous manner a labyrinth seal is achieved between the carrier part and the receiving vessel, whereby a gas-tightness can be achieved in a simple manner, with changing tolerances between these two.

If the cylindrical jacket in the region of the receiving space has inwardly directed barbs cooperating with the sealing lips, the carrier part can be held securely in its sealing position in the receiving vessel.

It is also advantageous if the carrier has a frusto-conical periphery matching a frusto-conical bore widening towards the open end in a projecting carrier part portion, whereby the carrier is held in the bore by a press fit, because a gradual assembly of the blood removal device is ensured in the mounting direction, i.e. in the direction of the central longitudinal axis. The cone angle is preferably between 1° and 4°.

BRIEF DESCRIPTION OF THE DRAWING

The invention is explained in further detail hereinbelow in connection with the presently preferred embodiments illustrated in the drawings, in which:

FIG. 2 shows the holding device according to FIG. 1 after the blood removal has been carried out, with the blood sample removal tubule removed, in side view, in section;

FIG. 3 shows the needle carrier with the cannula mounted therein according to FIGS. 1 and 2, in side view, in section and on an enlarged scale;

FIG. 5 shows a holding device with a further embodiment of the connection of the needle carrier with the receiving vessel and the blood sample removal tubule pushed on, in side view in section;

FIG. 6 shows the holding device according to FIG. 5 in front view, in section, along lines VI—VI in FIG. 5;

FIG. 7 shows the holding device according to FIGS. 5 and 6 with a separate position of the blood sample removal tubule from the cannula in side view in section;

FIG. 8 shows a further embodiment of the needle carrier with a cannula expressly mounted therein in side view, in section and in simplified diagrammatic illustration;

FIG. 9 shows another further development of the connection between receiving vessels and cannula in side view in section; and FIG. 10 shows a further embodiment of the receiving vessel with a cannula expressly mounted therein in side view in section.

DESCRIPTION OF THE PREFERRED EMBODIMENTS

Figure 1:
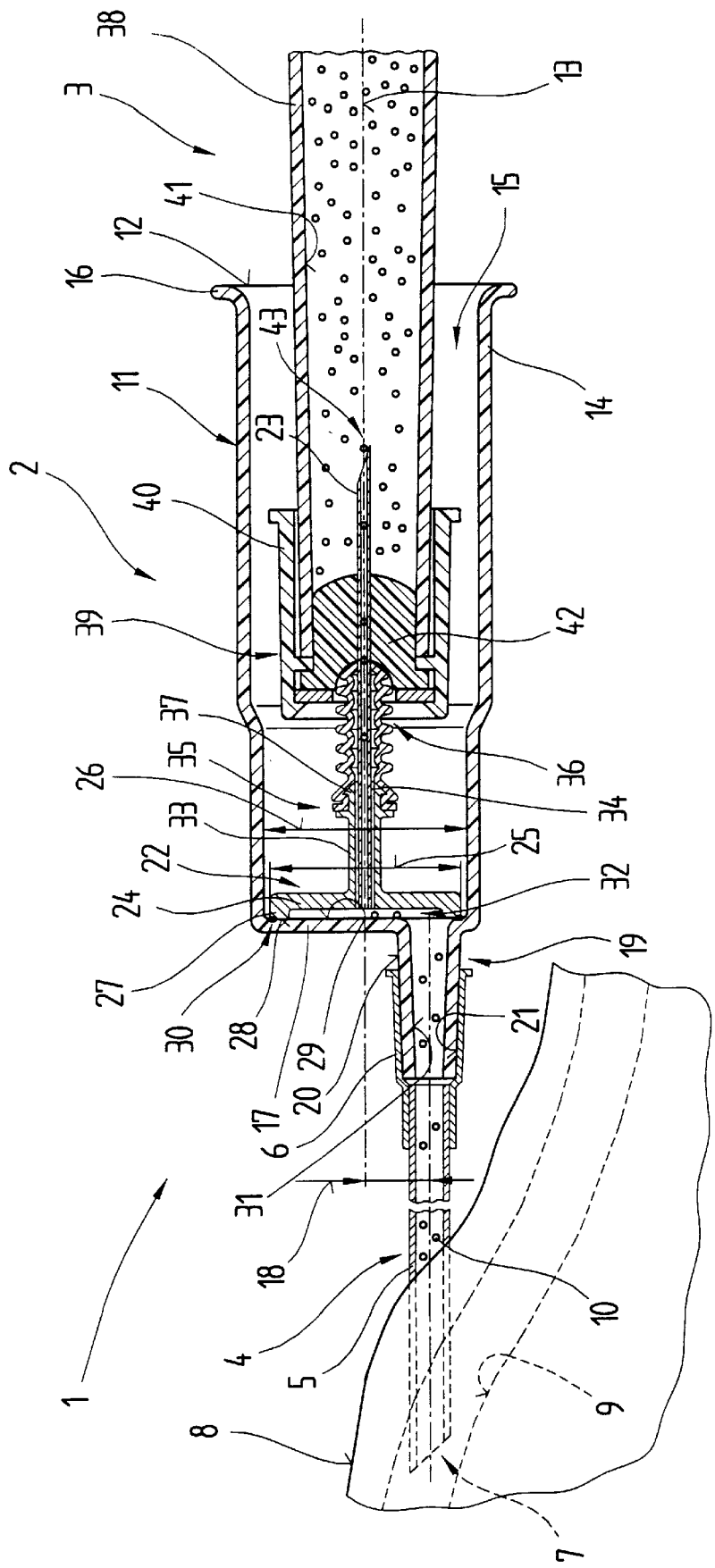
FIG. 1 shows a holding device constructed according to the invention with a cannula, a needle carrier and a blood sample removal tubule in the position of use in side view, in section.

In FIG. 1, a blood removal device 1 is shown, consisting of a holding device 2 for a blood sample removal tubule 3 and a needle arrangement 4 able to be coupled with the holding device 2. Needle arrangement 4 consists of a hollow removal needle 5 and a push-on part 6 arranged at one end.

An end 7 of removal needle 5 lying opposite push-on part 6 has a chamfer and forms a point, in order to facilitate the piercing into skin 8 of a patient, in order to be able to penetrate into a vein 9 and remove blood 10 therefrom, as is indicated diagrammatically by circles.

Holding device 2 consists of a receiving vessel 11, which has on a front side 12 lying opposite needle arrangement 4 an open front end to receive blood sample removal tubule 3. Receiving vessel 11 has a cylinder jacket 14 running concentrically to a central longitudinal axis 13 and thus forms a cylindrical receiving chamber 15. For easier operation of holding device 2, a handle 16 is formed on cylinder jacket 14 in the region of front side 12. Cylinder jacket 14 is closed off with a front wall 17 running perpendicularly to central longitudinal axis 13, in the region facing away from front side 12, i.e. in the region which faces needle arrangement 4.

On front wall 17, at a distance 18 eccentrically to central longitudinal axis 13, a holding part 19 in the shape of a circular ring is formed, narrowing in the direction of needle arrangement 4. Holding part 19 has on its outer periphery an outer cone 20 narrowing from front wall 17 in the direction of needle arrangement 4. Push-on part 6 of needle arrangement 4 has an inner cone 21 constructed reciprocally to outer cone 20, whereby with the coupling process between holding part 19 of holding device 2 and needle arrangement 4 a sealing connection is achieved. This connection is constructed so as to be gas-tight, as will be explained in further detail hereinbelow.

The construction of holding part 19 with its outer cone 20 or, respectively, push-on part 6 with its inner cone 21, can preferably take place in the form of a luer-cone connection with or without arresting. This type of connection is conventional prior art in medical technology. Of course, any other connection device known from the prior art can also be used to connect needle arrangement 4 with holding device 2.

In receiving chamber 15 of receiving vessel 11, in the region of front wall 17, needle holder 22 is arranged for the positioning of a cannula 23 which is constructed in the form of a hollow needle. Needle holder 22 in the present embodiment is formed in the region facing front wall 17 of holding device 2 by a carrier part 24 constructed in a disc shape, which has an outer diameter 25 which is smaller than an inner diameter 26 of receiving chamber 15 in the region of front wall 17. The difference between these two diameters is advantageously selected to be so great that even with differently occurring shrinkages of cylinder jacket 14, carrier part 24 can be pushed in, without difficulty and above all without jamming, into receiving chamber 15 until abutting against front wall 17.

Disc-shaped carrier part 24 has a circumferentially extending collar 27 projecting in the direction of front wall 17. End surface 28 of collar 27, running at right-angles to central longitudinal axis 13, faces needle arrangement 4, contacts a front wall surface 29 of front wall 17, and is connected in a gas-tight manner therewith by means of a preferably continuous weld seam 30, closed in itself, e.g. circular, preferably a high frequency weld seam. It is, of course, also possible to construct the connection of the two components in a gas-tight manner by means of a friction welding process or by an adhesive layer.

Holding part 19, narrowing conically and constructed in the form of a circular ring, has in its interior a through flow canal 31 which is in flow connection with a connecting canal 32, which runs between projecting collar 27 and front wall 17.

Needle holder 22 consists in turn of a needle carrier 33 constructed in the form of a circular ring, formed onto carrier part 24 and extending in the direction of open front side 12, in which needle carrier 33 cannula 23 is preferably mounted by means of an adhesive layer 34. However, the material of needle holder 22 may also be injection molded about cannula 23.

Needle carrier 33 of needle holder 22 has on its end facing open front side 12 of receiving vessel 11 a holding device 35 for a hose valve 36 constructed in the manner of a stocking, which valve 36 is formed by an elastic, fluid-tight protective covering, e.g. a highly elastic, self-closing silicon rubber for cannula 23. Holding device 35 for hose valve 36 has a holding nose 37 running around and projecting from needle carrier 33 and narrowing conically in the direction of front side 12 of receiving vessel 11. The conical widening, viewed in the direction of pushing the hose valve 36 over the holding nose, facilitates the slipping of the hose valve over the holding surface defined by holding nose 37 which extends perpendicularly to central longitudinal axis 12 and projects over needle carrier 33. The highly elastic hose valve 36 contracts with its open end behind the holding surface up to the diameter of needle carrier 33, whereby hose valve 36 is secured from unintentional pulling off the holding device 35.

Blood sample removal tubule 3 can be constructed, for example, in accordance with the date in WO 89/09735 and consists of a cylindrical housing 38 constructed open on one side, which is closed on the open front side by means of a gas-tight closure device 39. Closure device 39 consists in turn of a cap 40 overlapping housing 38 and of a plug 42 closing an interior 41 of housing 38. Interior 41 of blood sample removal tubule 3 closed with plug 42 is evacuated in the unused state, e.g. to a vacuum between 100 and 800 mbar.

In order to ensure an easy and reliable piercing of cannula 23 by plug 42 of blood sample removal tubule 3, cannula 23 has on the end facing front side 12 of receiving vessel 11 a chamfer, which, therefore, forms a point 43.

In the position of use of blood removal device 1 illustrated in FIG. 1, a conducting connection exists between vein 9 and evacuated interior 41 of blood sample removal tubule 3. This conducting connection is formed by hollow removal needle 5, through-flow canal 32 of holding part 19 adjoining thereto, connecting canal 32 between carrier part 24 and front wall 17 and the subsequent cannula 23 of hollow construction, which is mounted in needle holder 22 and the through-flow opening of which opens into interior 41 of blood sample removal tubule 3. The underpressure prevailing in blood sample removal tubule 3 serves to bridge the flow losses or flow resistances occurring in the conducting connection because otherwise the pressure prevailing in the veins is not sufficient o press into blood sample removal tubule 3 the blood 10 which is to be removed.

In the embodiment of blood sample removal tubule 3 illustrated here, which in the unused state has a vacuum in interior 41, it is crucial that the previously described components, which form the conducting connection between vein 9 and the interior of blood sample removal tubule 3, are constructed so as to be gas-tight, in order to thus guarantee a problem-free suction of blood 10 out from vein 9. Plug 42 of blood sample removal tubule 3, to be penetrated by cannula 23, is produced from a highly elastic and self-closing material, preferably pharmaceutical rubber or silicon rubber, in order to reliably seal interior 41 again after removal of blood sample removal tubule 3 from holding device 2.

In FIG. 2, blood removal device 1 is shown in a position in which blood sample removal tubule 3 is arranged at a distance from the position of cannula 23 illustrated in FIG. 1. Here, interior 41 of blood sample removal tubule 3 is sealed by automatically closing plug 42 with respect to the exterior environment and is filled with blood 10, indicated diagrammatically by circles.

Hose valve 36, constructed so as to be highly elastic, is expanded from the pushed together position shown in FIG. 1 in the direction of front side 12 of receiving vessel 11, and one end 44 of the elastic protective covering surrounds point 43 of cannula 23. Because the material of hose valve 36 is highly elastic and has high restoring values, the cut of point 43 of cannula 23 in end 44 closes automatically. Thereby, a sealing closure is achieved in the form of a valve action on the end of cannula 23 facing front side 12.

If a further removal of blood is now desired, a new blood sample removal tubule 3 with its evacuated interior 41 merely has to be pushed in again into receiving chamber 15 of receiving vessel 11 until plug 42 abuts end 44 of hose valve 36. On a further pushing in of blood sample removal tubule 3 in the direction of front wall 17, point 43 of cannula 23 pierces the end of hose valve 36 and penetrates through elastic plug 42 into interior 41 of blood sample removal tubule 3. Consequently, in turn, a conducting connection, sealed off towards the exterior, is ensured between vein 9 and interior 41 of blood sample removal tubule 3.

In FIG. 3, needle holder 22 is illustrated on an enlarged scale. Carrier part 24, constructed, for example, in disc-, piston- or plate form, extends perpendicularly to central longitudinal axis 13, with circumferentially extending annular collar 27 projecting from the side of carrier part 24 facing away from holding device 35. An extension 45 of circular ring shape and having a smaller circular ring width 46 than that of collar 27 projects from end face 28 of collar 27.

Circumferential extension 45 provides a continuous abutment surface against front wall surface 29 of receiving vessel 11, which through the smaller circular ring width 46 facilitates the connecting process which can take place, for example, by high frequency welding because thereby only a small amount of material has to be softened or melted on, in order to achieve a sealing abutment of collar end face 28 against front wall surface 29, preferably extending circumferentially. Of course, it is also possible, instead of the arrangement of collar 27 on carrier part 24, to construct the carrier part with a level surface and in the form of a plate or from a piston with, possibly, sealing elements inserted in its periphery, and to construct connecting canal 32 through a corresponding depression or convexity of front wall 17 in the direction of needle arrangement 4 and of removal needle 5.

Cannula 23 is glued in a sealing manner by means of adhesive layer 34 in needle carrier 33 of needle holder 22. It is, however, also possible to connect cannula 23 during the forming process of needle holder 22 in one piece therewith or to insert a needle carrier pre-heated over the conventional usage temperature and/or a cooled cannula one into the other and to then bring them to room temperature, whereby likewise a sealing shrink fit is able to be achieved between cannula 23 and needle holder 22.

As can be seen more clearly from the enlarged illustration of holding device 35, the end of holding nose 37 facing carrier part 24 has a diameter 47 to project from needle carrier 33. The circumferentially projecting holding nose 37 is constructed as a truncated cone 48 narrowing in the direction of point 43 of cannula 23 and serves hose valve 36 as a holding cone 49. To hold hose valve 36 better in position, holding device 35 has additionally a flange-shaped extension 51 spaced apart by a distance 50 from holding nose 37 in the direction of carrier part 24, which extension 51 likewise projects over diameter 47 of needle carrier 33 in a radial direction, i.e. perpendicularly to central longitudinal axis 13.

Hose valve 36, extending over cannula 23 and mounted on holding device 35, forms a sealing valve arrangement 52. Thereby, with blood sample removal tubule 3 removed, end 44 of hose valve 36 surrounds point 43 of cannula 23 and consequently seals off a through flow opening 53 of cannula 23 with respect to receiving chamber 15 of receiving vessel 11. Thereby, the conducting connection already described previously between end 7 of needle arrangement 4 and point 43, facing open front side 12 of receiving vessel 11, of cannula 43 is closed off in a sealing manner.

Figure 4:
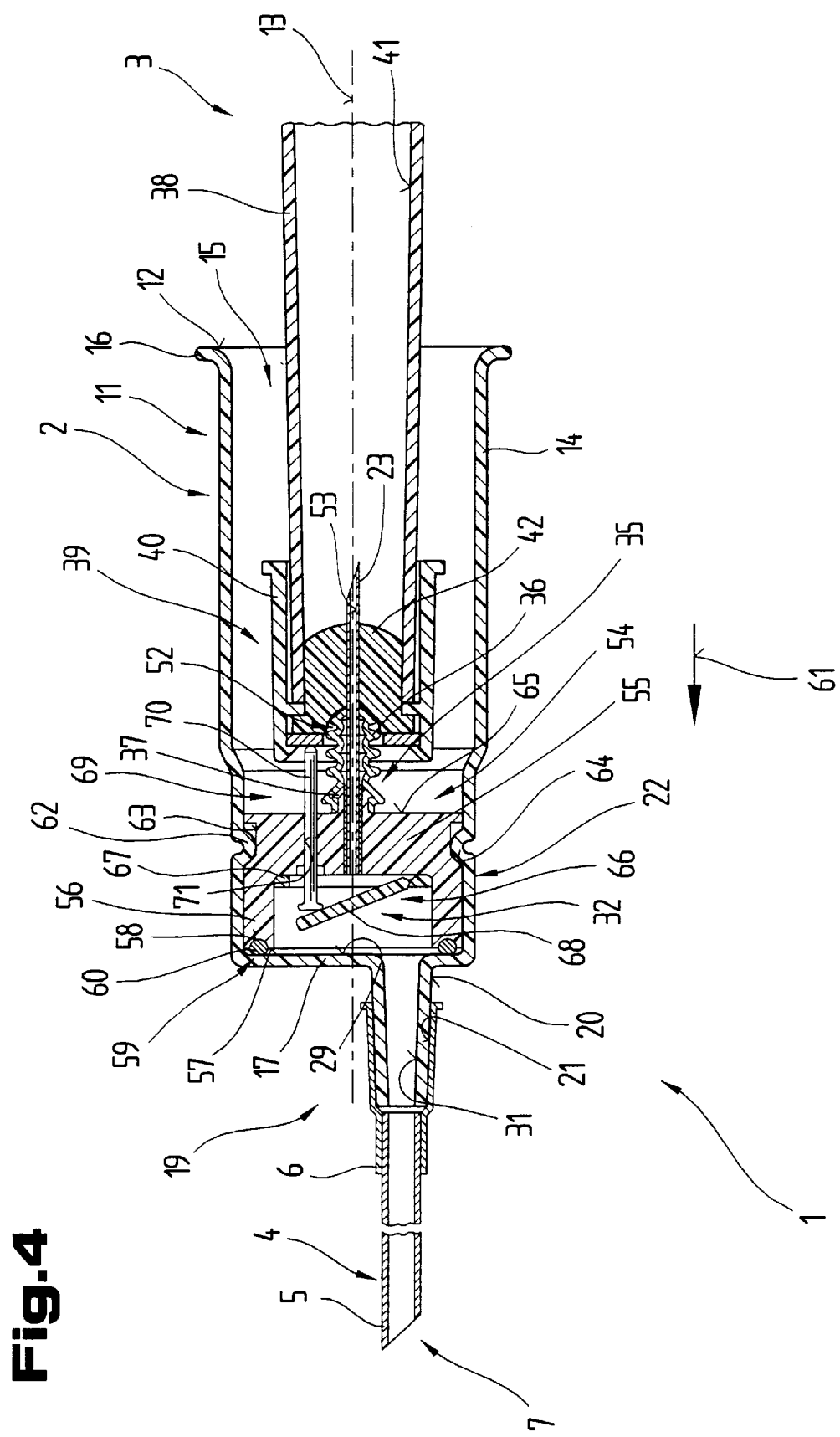
FIG. 4 shows a holding device with a different embodiment of the needle carrier and an additional closure device in the duct connection in side view, in section and in simplified, diagrammatic illustration.

In FIG. 4, another embodiment of blood removal device 1 is shown with holding device 2 and blood sample removal tubule 3, in which the same reference numbers have been used for identical parts.

Blood sample removal tubule 3 consists of housing 38, closed on one side, closure device 39, consisting of cap 40 and plug 42, closing interior 41 in a sealing manner.

Holding device 2 for cannula 23 is formed by receiving vessel 11, closed on one side with front wall 17, holding part 19, formed eccentrically to central longitudinal axis 13 on front wall 17, with its outer cone 20 and handle 16 arranged on open front side 12. On holding part 18, in turn, needle arrangement 4 is mounted, consisting of hollow removal needle 5 and push-on part 6 with its inner cone 21.

Needle holder 22 for cannula 23 deviates from the previously described embodiment and is constructed as a pot-shaped carrier part 54 and consists of a disc-shaped holding wall 55, on which a projection 56 is formed which is constructed in the form of a circular ring.

Circumferentially extending hemispherical recess 58 in end face 57 facing front wall surface 29 of front wall 17 serves to receive a sealing element 59 such as, for example, an O-ring 60. Owing to the elastically deformable sealing element 59 and the cavity formed by projection 56, in turn the connecting canal 32 is produced, in flow connection with through flow canal 31, whereby likewise a sealing connection is ensured between needle holder 22 and receiving vessel 11.

In order to ensure an exact positioning or mounting of carrier part 54 in receiving vessel 11 or to bring about a sealing transition between front wall surface 29 and end face 57, needle holder 22 is pressed in the direction of arrow 61 against front wall surface 29, whereby sealing element 59 deforms and then in this position, cylinder jacket 14 is pressed in thermally and deforms to produce bead 62 projecting into a holding groove 63 formed on the outer periphery of holding wall 55. This bead 62 rests against a holding surface 64 which is widened conically in the direction of end face 57, whereby prestressed sealing element 59 on the one hand seals connecting canal 32 towards the exterior and on the other hand presses holding surface 64 against bead 62 and thus represents a secured fixing in position.

On a front side 65 of needle holder 22, facing front side 12 of receiving vessel 11, in turn holding device 35 for hose valve 36 of valve arrangement 52 is arranged. Holding device 35 consists in turn of holding nose 37 previously described, which is constructed in the form of a truncated cone. The longitudinal stop for hose valve 36 in the direction of front wall 17 is formed by front surface 65 in this embodiment.

In addition to valve arrangement 52, in connecting canal 32 formed by projection 56, an additional closure device 66 is arranged. This consists of an insert part 67 which is inserted in a sealing manner in the connecting canal 32 and of a flap 68, connected articulatedly and in one piece therewith, which closes off the through flow opening 53 of cannula 23 with respect to connecting canal 32. The adjustment of the flap takes place through an actuating device 69, which is formed by a push rod 70.

In the position of use of blood removal device 1 illustrated in FIG. 4, a part of closure device 39 of blood sample removal tubule 3 lies against the end of push rod 70 facing front side 12, whereby this push rod 70 is pushed in an opening 71 arranged in the holding wall 55 in the direction of central longitudinal axis 13, and on further pushing in of blood sample removal tubule 3 into receiving chamber 15, the end which faces front wall 17 brings flap 68 into the opened position which is shown. If blood sample removal tubule 3 is removed from receiving chamber 15 after the removal of blood has been completed, the blood situated in needle arrangement 4 presses flap 68 together with push rod 70 into a closed position again, whereby the conducting connection between connecting canal 32 and through flow opening 53 in cannula 23 is interrupted.

In FIGS. 5 to 7, another embodiment of blood removal device 1 is illustrated, in which carrier part 24 of needle holder 22 in holding device 2 is constructed in a pot shape and its closed front wall 72 faces front wall 17 of receiving vessel 11.

This front wall 72 is provided with a concave depression 73, which between front wall 17 and front wall 72 forms a connecting canal 32 between the through flow opening 53 of cannula 23 and holding part 19 and also needle arrangement 4.

Concentric to the cylinder walls of pot-shaped carrier part 24, needle carrier 33 for cannula 23 is arranged.

Cannula 23 can be secured in needle carrier 33 by means of an adhesive layer or, for example, can be formed directly into carrier part 24.

At the end of needle carrier 33 facing away from front wall 72, holding device 35 for hose valve 36 is arranged.

The fastening of a fluid-tight casing 74 in stocking form, which forms hose valve 36, consists, for example, of a pharmaceutical rubber or a highly elastic silicon rubber, which has a very high restoring capacity in the case of deformations or separations. Hence, as is shown in FIG. 5, on pushing a blood sample removal tubule 3 into receiving vessel 11 or its receiving chamber 15, casing 74 is folded together or pushed together through plug 42 into the position shown in FIG. 5, so that cannula 23 penetrates plug 42.

Since plug 42 of closure device 39 also consists of a material with a very high elastic restoring force, so that on removal of cannula 23 out of interior 41 of blood sample removal tubule 3 the opening of cannula 23 facing interior 41 is already closed or is separated from the vacuum contained in blood sample removal tubule 3, so that the subsequent suction of body fluid, in particular blood 10, via through flow opening 53 of cannula 23 ia already prevented and on complete removal of blood sample removal tubule 3 from cannula 23, the opened front end of cannula 23 is then immediately surrounded by stocking-shaped casing 74 and hence an emergence of body fluid or blood 10 is prevented.

The position of stocking-shaped casing 74, in which a passage of blood 10 from through-flow opening 53 in the direction of receiving chamber 15 is prevented, is shown in FIG. 7. In order to ensure a stable mounting of needle carrier 33 concentrically in pot-shaped carrier part 24, between the latter and a cylindrical outer jacket 75 of carrier part 24 a plurality of radial cross-pieces 76 is provided, arranged distributed over the periphery of needle carrier 33.

Hence, even with the action of high eccentric forces during the pushing in of blood sample removal tubule 3, a secure and accurately positioned mounting of cannula 23 can be achieved approximately in the central region, i.e. in the region of central longitudinal axis 13 of receiving chamber 15.

These cross-pieces 76 reinforce outer jacket 75 especially during the pressing in of carrier part 24 in a narrowed receiving space 77 with respect to receiving chamber 15.

With a corresponding construction of the surface or of the diameter of outer jacket 75 and of receiving space 77, a press fit can be achieved between receiving space 77 and carrier part 24. If this press fit is not sufficient to ensure an air-tight closure between cylinder jacket 14 and carrier part 24, then in the region of the contact surfaces in addition an air-tight adhesive layer can be arranged, preferably extending circumferentially.

However, it would also be possible, for example by the introduction of electrodes between outer jacket 75 and cylinder jacket 14, as indicated diagrammatically by a circumferential weld seam 30, to weld these together in a gas-tight and fluid-tight manner.

In FIG. 8, another embodiment is shown, which corresponds in its construction substantially to the embodiment illustrated in FIGS. 5 to 7. Therefore, the same reference numbers are used for identical parts.

The embodiments according to FIGS. 5 to 7 and FIG. 8 differ in that cannula 23, which is in turn surrounded by a hose valve 36, is mounted in a cone-shaped holder 78 by gluing in or injection molding the holder. This holder 78 has an outer cone 79 narrowing in the direction of front wall 17 of receiving vessel 11 of holding device 2, which outer cone 79 has a very small cone angle 80 of, for example, 0.5 to 4°, preferably 1°.

This holder 78 with its outer cone 79 is pressed in an inner cone 81 of a through opening 82 in carrier part 24. Thereby, holder 78 is held secure with cannula 23 owing to cone angle 80 by means of a pres fit, which owing to cone angle 80 is self-locking. It is additionally possible, if necessary, for the gas-tight connection of holder 78 with carrier part 24, to use a corresponding gas-tight adhesive layer or to arrange an O-ring or another type of sealing ring in holder 78 or in carrier part 24.

A length 83 of the truncated cone of holder 78 is slightly smaller here than a depth 84 of through opening 82. The truncated cone of holder 78 is furthermore delimited by a stop flange 85.

A root circle diameter of through opening 82, facing stop flange 85, is preferably slightly smaller than the root circle diameter of the truncated cone of holder 78 in the region of stop flange 85.

This prevents stop flange 85 from contacting a tubular extension 86, which has through opening 82, before a clamping- or press fit has occurred between holder 78 and tubular extension 86 and its through opening 82. Moreover, through the selection of length 83 of the truncated cone of holder 78, it is ensured that the latter cannot project into connecting canal 32 and, above all, cannot lie against end wall 17 of receiving vessel 11. Thereby it is ensured that always a fluid passage exists between cannula 23 and connecting canal 32.

Furthermore, in this embodiment, there is shown a further development which, however, can be independent of the construction of needle holder 22 and of carrier part 24, which makes possible a gas-tight, undetachable mounting of carrier part 24 in receiving space 77.

For the gas-tight closure and for the mounting of carrier part 24, the latter is provided on the peripheral surface of outer jacket 75 with circumferential sealing lips 87 which in the relaxed state have a somewhat greater diameter than the inner diameter 26 of receiving space 77. Thereby, after the insertion of carrier part 24 into receiving space 77, these sealing lips 87 are deformed and extend over the entire periphery in the manner of a labyrinth seal against cylinder jacket 14 of receiving vessel 11.

In order to ensure a sufficiently secure fit and a mounting of carrier part 24 in receiving space 77, receiving space 77 can be provided on its surface facing carrier part 24, at least in the end region facing cannula 23, with projecting holding cross-pieces 88 constructed in the form of barbs, which can also extend circumferentially over the entire periphery of receiving space 77. Thereby, on pushing in of carrier part 24 into receiving space 77, sealing lips 87 spread themselves against the vertical supporting walls of holding cross-pieces 88 and, therefore, an automatic locking or arresting is achieved against a removal of carrier part 24 out from receiving space 77.

In FIGS. 9 and 10, further possibilities are shown for the fastening of holder 78 for cannula 23 in receiving vessel 11 of holding device 2.

Thus, in the embodiment according to FIG. 9, holder 78 is inserted directly into a through opening 82, which is arranged in a tubular extension 86 which, in turn, is formed in one piece onto cylinder jacket 14. This through opening 82, as described with the aid of the embodiment in FIG. 8 with carrier part 24, is provided with a corresponding inner cone 81, into which outer cone 79 of holder 78 engages and is mounted therein by means of a press fit, especially with a corresponding construction of the outer and inner cones as self-locking cones.

The construction of hose valve 36 again corresponds to the previously described embodiments in which the fastening of hose-shaped casing 74 can take place in that the latter is slipped over an encircling collar 89, which can also be constructed in a cone shape and has an undercut 90.

If this mechanical fixing of casing 74 by the use of the elastic prestressing of casing 74 is not sufficient, a mounting can take place additionally by means of an adhesive seam or an adhesive layer.

In the embodiment according to FIG. 10, the inner cone 81 to receive the outer cone 79 of holder 78 is achieved through a corresponding shaping of receiving space 77. In this case, receiving space 77 continues directly into through flow canal 31 of holding part 19 for needle arrangement 4. The embodiment of hose valve 36 also in this embodiment corresponds to the previously described embodiments.

Furthermore, in this embodiment, it is indicated that in addition to the outer and inner cones 79, 81, which lead to a gas-tight connection between cylinder jacket 14 and holder 78, a form-fitting connection is also created, for example by a chemical connection of the materials of cylinder jacket 14 and of holder 78.

This is possible, for example, in that before the pressing in of holder 78 into inner cone 81, into cylinder jacket 14 on outer cone 79, for example, a solvent dissolving the plastic of holder 78 and/or of cylinder jacket 14 is applied preferably continuously right around, so that after the pressing in of holder 78 a form-fitting connection occurs, using the adhesive effect of the softened plastic materials. Thereby, a firm fit of holder 78 is achieved, independently of the press fit which is achieved and, above all, a fluid-tight closure is achieved right around between cylinder jacket 14 and holder 78.

In addition, it can be seen in FIG. 7 that between holding part 19 and a region of cylinder jacket 14 lying closest thereto, a circumferential bearing surface 91 of carrier part 24 extends substantially perpendicularly to central longitudinal axis 13. Through this construction, even with a removal needle inserted eccentric to central longitudinal axis 13 of receiving vessel 11, a full and gas-tight closure is achieved between carrier part 24 and receiving vessel 11.

Of course, in the illustrated embodiments, it is possible, even if this is not expressly mentioned, to connect between carrier part 24 and extension 86 or of receiving vessel 11 in the direction towards central longitudinal axis 13, a displacement-proof mounting of these parts by means of adhesive layers or weld seams 30, for example high-frequency welds.

In addition, it is possible to soften the plastic by means of solvents so that with the use of the adhesive effect inherent in plastic, it is possible to connect these parts with each other, in particular in a gas-tight manner. It has been shown to be advantageous if needle holer 22 including carrier part 24 and/or receiving vessel 11 consist of plastic, in particular polypropylene.

In order to achieve this gas-tightness from needle arrangement 4 up to interior 41 of blood sample removal tubule 3, it must be guaranteed that all components and also the individual weld or connection sites between these components have corresponding characteristics. This is also to be taken into account in the selection of the individual materials.

Finally, it is to be pointed out that in the illustration of the preferred embodiments, for a better understanding of the function of the devices according to the invention and for a simplified representation, proportions are distorted and some are illustrated not to scale.

Individual parts of the devices shown in the individual embodiments, i.e. either each embodiment in itself or else individual different features from the various embodiments in any desired combination with each other can also form independent solutions in accordance with the invention.

In particular, the individual embodiments shown in FIGS. 1, 2, 3; 4; 5, 6, 7; 8; 9; 10 can also form the subject matter of independent solutions in accordance with the invention. The problems and solutions in this respect according to the invention are to be taken from the detailed descriptions of these figures.

I claim:

1. A holding device for a blood sample removal tubule, comprising
   (a) a receiving vessel comprising
      (1) a cylindrical jacket having a central longitudinal axis and an open end, and
      (2) a front wall closing an end of the receiving vessel opposite the open end,
      (3) the cylindrical jacket and the front wall defining a receiving chamber,
   (b) a holding part connected to the front wall of the receiving vessel and projecting therefrom in a direction facing away from the cylindrical jacket, the holding part being arranged eccentrically with respect to the central longitudinal axis and defining a flow-through canal, (c) a cannula having one end facing the front wall of the receiving vessel and an opposite end facing the open end of the receiving vessel, the cannula defining a flow-through bore, (d) a holder for the cannula, the holder comprising
  (1) a carrier part having a periphery connected to the receiving vessel in a gas- and fluid-tight manner by means extending along the periphery of the carrier part, and
  (2) a carrier holding the cannula in a fixed position and in a gas- and fluid-tight manner, the opposite end of the cannula projecting beyond the carrier,
  (3) the carrier part of the holder and the front wall of the receiving vessel defining a connecting canal therebetween, the connecting canal connecting the flow-through canal of the holding part with the flow-through bore of the cannula, and (e) a selectively openable valve arrangement arranged between the connecting canal and the receiving chamber, the valve arrangement comprising
  (1) a hose valve arranged between the cannula and the receiving chamber, and
  (2) a flap valve arranged between the cannula and the connecting canal.

2. The holding device of claim 1, wherein the means extending along the periphery of the carrier part is a weld seam.

3. The holding device of claim 1, wherein the means extending along the periphery of the carrier part is an adhesive layer.

4. The holding device of claim 1, wherein the hose valve is a fluid-tight casing having the shape of a stocking.

5. The holding device of claim 4, further comprising a holding device on an end of the carrier facing the open end of the receiving vessel for retaining an open end of the fluid-tight casing.

6. The holding device of claim 5, wherein the holding device is a frusto-conical holding nose tapering inwardly towards-the open end of the receiving vessel.

7. The holding device of claim 1, wherein the receiving chamber has a receiving space for the carrier part of the holder and the carrier part is securely held in the receiving space.

8. The holding device of claim 7, wherein the carrier part is securely held in the receiving space by a friction fit.

9. The holding device of claim 7, wherein the carrier part is securely held in the receiving space by an adhesive layer.

10. The holding device of claim 1, wherein the carrier part of the holder has a cylindrical portion projecting from a circumference of the carrier part towards the open end of the cylindrical jacket along an inner surface of the cylindrical jacket, and further comprising gas-tight means connecting the cylindrical carrier part portion to the cylindrical jacket.

11. The holding device of claim 1, further comprising a bearing surface for the carrier part of the holder, the bearing surface extending substantially perpendicularly to the central longitudinal axis between the flow-through canal of the holding part and the cylinder jacket.

12. A holding device for a blood sample removal tubule, comprising
  (a) a receiving vessel comprising
    (1) a cylindrical jacket having a central longitudinal axis and an open end, and
    (2) a front wall closing an end of the receiving vessel opposite the open end,
    (3) the cylindrical jacket and the front wall defining a receiving chamber,
  (b) a holding part connected to the front wall of the receiving vessel and projecting therefrom in a direction facing away from the cylindrical jacket, the holding part being arranged eccentrically with respect to the central longitudinal axis and defining a flow-through canal,
  (c) a cannula having one end facing the front wall of the receiving vessel and an opposite end facing the open end of the receiving vessel, the cannula defining a flow-through bore,
  (d) a holder for the cannula, the holder comprising
    (1) a carrier part having a periphery connected to the receiving vessel in a gas- and fluid-tight manner by means extending along the periphery of the carrier part, and
    (2) a carrier holding the cannula in a fixed position and in a gas- and fluid-tight manner, the opposite end of the cannula projecting beyond the carrier,
    (3) the carrier part of the holder comprising a portion projecting therefrom towards the open end of the receiving vessel, the projecting carrier part portion defining a frusto-conical bore widening towards the open end, and the carrier being held in the frusto-conical bore and having a stop flange, the bore having a length exceeding that of the carrier, and
    (4) the carrier part of the holder and the front wall of the receiving vessel defining a connecting canal therebetween, the connecting canal connecting the flow-through canal of the holding part with the flow-through bore of the cannula, and
  (e) a selectively openable valve arrangement arranged between the connecting canal and the receiving chamber, the valve arrangement comprising
    (1) a hose valve arranged between the cannula and the receiving chamber.

13. The holding device of claim 12, wherein the carrier has a frusto-conical periphery matching the frusto-conical bore whereby the carrier is held in the bore by a press fit.

14. The holding device of claim 13, wherein the cone angle is between 1° and 4°.

15. A holding device for a blood sample removal tubule, comprising
  (a) a receiving vessel comprising
    (1) a cylindrical jacket having a central longitudinal axis and an open end, and
    (2) a front wall closing an end of the receiving vessel opposite the open end,
    (3) the cylindrical jacket and the front wall defining a receiving chamber,
  (b) a holding part connected to the front wall of the receiving vessel and projecting therefrom in a direction facing away from the cylindrical jacket, the holding part being arranged eccentrically with respect to the central longitudinal axis and defining a flow-through canal,
  (c) a cannula having one end facing the front wall of the receiving vessel and an opposite end facing the open end of the receiving vessel, the cannula defining a flow-through bore,
  (d) a holder for the cannula, the holder comprising
    (1) a carrier part having a periphery connected to the receiving vessel in a gas- and fluid-tight manner by means extending along the periphery of the carrier part, and
    (2) a carrier holding the cannula in a fixed position and in a gas- and fluid-tight manner, the opposite end of the cannula projecting beyond the carrier, (3) the carrier part of the holder and the front wall of the receiving vessel defining a connecting canal therebetween, the connecting canal connecting the flow-through canal of the holding part with the flow-through bore of the cannula,
(e) the receiving chamber having a receiving space for the carrier part of the holder and the carrier part being securely held in the receiving space,
(f) the carrier part having peripheral sealing lips extending in a radial direction, the sealing lips in a relaxed state having and outer diameter exceeding an inner diameter of the receiving space, and
(g) a selectively openable valve arrangement arranged between the connecting canal and the receiving chamber, the valve arrangement comprising
    (1) a hose valve arranged between the cannula and the receiving chamber.

16. The holding device of claim 15, wherein the cylindrical jacket in the region of the receiving space has inwardly directed barbs cooperating with the sealing lips.

17. A holding device for a blood sample removal tubule, comprising
(a) a receiving vessel comprising
    (1) a cylindrical jacket having a central longitudinal axis and an open end, and
    (2) a front wall closing an end of the receiving vessel opposite the open end, a portion of a side of the front wall closest to the cylindrical jacket and facing the open end thereof defining a peripheral bearing surface extending perpendicularly to the longitudinal axis,
    (3) the cylindrical jacket and the front wall defining a receiving chamber,
(b) a holding part connected to the front wall of the receiving vessel and projecting therefrom in a direction facing away from the cylindrical jacket, the holding part being arranged eccentrically with respect to the central longitudinal axis and defining a flow-through canal,
(c) a cannula having one end facing the front wall of the receiving vessel and an opposite end facing the open end of the receiving vessel, the cannula defining a flow-through bore,
(d) a holder for the cannula, the holder comprising
    (1) a disc-shaped carrier part having an outer diameter defining a periphery which is smaller than an inner diameter of an adjacent portion of the cylindrical jacket of the receiving vessel,
    (2) an annular collar at the periphery of the carrier part and projecting therefrom towards the front wall of the receiving vessel, the collar having an end surface connected to the peripheral bearing surface of the front wall of the receiving vessel in a gas- and fluid-tight manner by a continuous weld seam,
    (3) the carrier part with the annular collar and the front wall of the receiving vessel defining a connecting canal therebetween, the connecting canal connecting the flow-through canal of the holding part with the flow-through bore of the cannula, and
    (4) a carrier holding the cannula in a fixed position and in a gas- and fluid-tight manner, the opposite end of the cannula projecting beyond the carrier, and
(e) a selectively openable valve arrangement arranged between the connecting canal and the receiving chamber, the valve arrangement comprising
    (1) a hose valve arranged between the cannula and the receiving chamber.

18. The holding device of claim 17, wherein the holder is arranged concentrically about the central longitudinal axis.

19. The holding device of claim 17, wherein the flow-through canal of the holding part opens into the connecting canal in an area defined by the annular collar.

20. The holding device of claim 17, further comprising a circular extension projecting from the end surface of the collar in a direction facing away from the carrier part.

* * * * *